US008986719B2

(12) United States Patent
Piergallini et al.

(10) Patent No.: US 8,986,719 B2
(45) Date of Patent: Mar. 24, 2015

(54) TEETH WHITENING COMPOSITIONS AND METHODS

(75) Inventors: Remigio Piergallini, Grottammare Ascoli Piceno (IT); Nikolaos Loupis, Athens (GR)

(73) Assignee: KLOX Technologies Inc., Laval (CA)

(*) Notice: Subject to any disclaimer, the term of this patent is extended or adjusted under 35 U.S.C. 154(b) by 0 days.

(21) Appl. No.: 13/484,151

(22) Filed: May 30, 2012

(65) Prior Publication Data

US 2012/0237580 A1 Sep. 20, 2012

Related U.S. Application Data

(63) Continuation of application No. 13/296,007, filed on Nov. 14, 2011, which is a continuation of application No. 11/598,206, filed on Nov. 9, 2006, now Pat. No. 8,075,875.

(60) Provisional application No. 60/735,072, filed on Nov. 9, 2005.

(51) Int. Cl.
A61K 8/49 (2006.01)
A61Q 11/00 (2006.01)
A61K 8/02 (2006.01)
A61K 8/22 (2006.01)

(52) U.S. Cl.
CPC . *A61K 8/22* (2013.01); *A61K 8/498* (2013.01); A61K 2800/43 (2013.01); A61K 2800/81 (2013.01); A61K 2800/434 (2013.01); *A61Q 11/00* (2013.01)
USPC ............... 424/401; 424/49; 424/53

(58) Field of Classification Search
CPC .......... A61K 8/22; A61K 8/498; A61O 11/00
USPC ................. 252/186.39; 424/53; 510/100, 117
See application file for complete search history.

(56) References Cited

U.S. PATENT DOCUMENTS

| | | | |
|---|---|---|---|
| 2,877,221 A | 3/1959 | Lanbach | |
| 3,293,127 A * | 12/1966 | Beck | 424/75 |
| 3,372,125 A * | 3/1968 | Hill | 510/117 |
| 3,595,798 A | 7/1971 | Smith et al. | |
| 3,652,420 A | 3/1972 | Hill | |
| 3,728,446 A | 4/1973 | Roberts et al. | |
| 4,574,097 A * | 3/1986 | Honeycutt | 428/36.1 |
| 4,891,211 A | 1/1990 | Winston | |
| 4,992,256 A | 2/1991 | Skaggs et al. | |
| 5,658,148 A | 8/1997 | Neuberger et al. | |
| 5,749,968 A | 5/1998 | Melanson et al. | |
| 5,785,527 A | 7/1998 | Jensen et al. | |
| 5,844,016 A | 12/1998 | Sawhney et al. | |
| 5,858,332 A | 1/1999 | Jensen et al. | |
| 5,922,331 A | 7/1999 | Mausner | |
| 6,030,222 A | 2/2000 | Tarver | |
| 6,036,493 A | 3/2000 | Sharma | |
| 6,056,548 A | 5/2000 | Neuberger et al. | |
| 6,084,005 A | 7/2000 | Fukunishi et al. | |
| 6,107,466 A | 8/2000 | Hasan et al. | |
| 6,121,341 A * | 9/2000 | Sawhney et al. | 522/84 |
| 6,149,895 A | 11/2000 | Kutsch | |
| 6,162,055 A | 12/2000 | Montgomery et al. | |
| 6,254,388 B1 | 7/2001 | Yarborough | |
| 6,267,976 B1 | 7/2001 | Barnhart et al. | |
| 6,337,357 B1 | 1/2002 | Fukunishi et al. | |
| 6,343,933 B1 | 2/2002 | Montgomery et al. | |
| 6,361,329 B1 | 3/2002 | Dekker et al. | |
| 6,365,134 B1 | 4/2002 | Orlowski et al. | |
| 6,387,353 B1 | 5/2002 | Jensen et al. | |
| 6,391,283 B1 | 5/2002 | Jensen et al. | |
| 6,420,455 B1 | 7/2002 | Landgrebe et al. | |
| 6,440,396 B1 | 8/2002 | McLaughlin | |
| 6,444,725 B1 | 9/2002 | Trom et al. | |
| 6,475,497 B1 | 11/2002 | Rajaiah et al. | |
| 6,485,709 B2 | 11/2002 | Banerjee et al. | |
| 6,488,914 B2 | 12/2002 | Montgomery | |
| 6,514,543 B2 | 2/2003 | Montgomery | |
| 6,528,555 B1 | 3/2003 | Nikutowski et al. | |
| 6,536,628 B2 | 3/2003 | Montgomery | |
| 6,541,460 B2 | 4/2003 | Petito | |
| 6,558,653 B2 | 5/2003 | Andersen et al. | |
| 6,846,182 B1 | 1/2005 | Sibner | |
| 6,905,672 B2 | 6/2005 | Rajaiah et al. | |
| 6,960,079 B2 | 11/2005 | Brennan et al. | |
| 7,220,438 B2 | 5/2007 | Quintanilla Almagro et al. | |

(Continued)

FOREIGN PATENT DOCUMENTS

CA 2 222 027 A1 6/1998
CA 2 551 613 12/2005

(Continued)

OTHER PUBLICATIONS

Fischersci, "Material Safty Data Sheet: Sodium acetate buffer". https://fscimage.fishersci.com/msds/91502.htm (Apr. 13, 2000).*

(Continued)

*Primary Examiner* — Walter Webb
(74) *Attorney, Agent, or Firm* — Ropes & Gray LLP

(57) ABSTRACT

Disclosed herein are teeth whitening compositions generally including an oxidizing agent (e.g., a peroxide), and an activating agent that has an emission wavelength between about 400 nm and about 570 nm (e.g., Eosin B). Methods of employing these compositions to whiten teeth, methods of making these compositions and kits that include some or part of the composition ingredients, are also described.

10 Claims, No Drawings

(56) References Cited

U.S. PATENT DOCUMENTS

| | | | |
|---|---|---|---|
| 7,314,470 | B2 | 1/2008 | Malodobry |
| 7,354,448 | B2 | 4/2008 | Altshuler et al. |
| 8,075,875 | B2 | 12/2011 | Piergallini et al. |
| 8,632,822 | B2 | 1/2014 | Piergallini et al. |
| 8,637,086 | B2 | 1/2014 | Piergallini et al. |
| 8,658,219 | B2 | 2/2014 | Piergallini et al. |
| 8,685,466 | B2 | 4/2014 | Piergallini et al. |
| 2001/0022970 | A1 | 9/2001 | Dees et al. |
| 2003/0133940 | A1 | 7/2003 | Dees et al. |
| 2003/0198605 | A1 | 10/2003 | Montgomery |
| 2004/0136971 | A1 | 7/2004 | Scharp et al. |
| 2004/0191330 | A1 | 9/2004 | Keefe et al. |
| 2005/0026298 | A1 | 2/2005 | Bickett et al. |
| 2005/0049228 | A1 | 3/2005 | Albrecht et al. |
| 2005/0059731 | A1 | 3/2005 | Albrecht et al. |
| 2005/0123588 | A1 | 6/2005 | Zhu et al. |
| 2006/0198796 | A1 | 9/2006 | Giniger et al. |
| 2006/0287211 | A1 | 12/2006 | Barbizan et al. |
| 2007/0092469 | A1 | 4/2007 | Jacobs |
| 2007/0128132 | A1 | 6/2007 | Piergallini et al. |
| 2007/0166369 | A1 | 7/2007 | Neuberger et al. |
| 2007/0244195 | A1 | 10/2007 | Burkhart et al. |
| 2008/0108681 | A1 | 5/2008 | Scimeca et al. |
| 2008/0113037 | A1 | 5/2008 | Green et al. |
| 2008/0206159 | A1 | 8/2008 | Tamarkin et al. |
| 2008/0305101 | A1 | 12/2008 | Ruoslahti et al. |
| 2010/0266989 | A1 | 10/2010 | Piergallini et al. |
| 2011/0218482 | A1 | 9/2011 | Piergallini et al. |
| 2011/0224599 | A1 | 9/2011 | Piergallini et al. |

FOREIGN PATENT DOCUMENTS

| | | |
|---|---|---|
| CA | 2 580 381 | 1/2006 |
| EP | 0 380 157 B1 | 8/1990 |
| EP | 0 704 539 A2 | 4/1996 |
| EP | 1 235 543 A1 | 9/2002 |
| EP | 1 235 544 A1 | 9/2002 |
| EP | 1 749 532 A1 | 2/2007 |
| EP | 1 779 891 A1 | 5/2007 |
| EP | 1 951 184 A2 | 8/2008 |
| EP | 2 338 465 A1 | 6/2011 |
| JP | 01-279838 | 10/1989 |
| JP | 02-233612 | 9/1990 |
| JP | 03-169805 A | 7/1991 |
| JP | 10-182390 A | 7/1998 |
| JP | 10-330235 | 12/1998 |
| JP | 2001-511137 A | 8/2001 |
| JP | 2002-502864 A | 1/2002 |
| JP | 2002-226349 A | 8/2002 |
| JP | 2002-293747 A | 10/2002 |
| JP | 2003-339875 | 12/2003 |
| JP | 04-219756 B2 | 2/2009 |
| WO | WO-81/00513 A1 | 3/1981 |
| WO | WO 90/09779 A1 | 9/1990 |
| WO | WO 91/02530 A | 7/1991 |
| WO | WO 97/21420 A1 | 6/1997 |
| WO | WO 98/10738 A1 | 3/1998 |
| WO | WO 98/11827 A1 | 3/1998 |
| WO | WO 98/23219 A1 | 6/1998 |
| WO | WO 98/30169 A1 | 7/1998 |
| WO | WO-98/33761 A1 | 8/1998 |
| WO | WO-99/39238 A1 | 8/1999 |
| WO | WO-99/40870 | 8/1999 |
| WO | WO 99/40870 A1 | 8/1999 |
| WO | WO-99/49823 A1 | 10/1999 |
| WO | WO 99/63900 A1 | 12/1999 |
| WO | WO 01/00190 A2 | 1/2001 |
| WO | WO 01/12181 A1 | 2/2001 |
| WO | WO 02/22097 A1 | 3/2002 |
| WO | WO-03/000215 A1 | 1/2003 |
| WO | WO 03/017824 A2 | 3/2003 |
| WO | WO-03/061696 A2 | 7/2003 |
| WO | WO-03/099247 A1 | 12/2003 |
| WO | WO 2004/028498 A1 | 4/2004 |
| WO | WO-2004/081222 A2 | 9/2004 |
| WO | WO-2005/009604 A1 | 2/2005 |
| WO | WO-2005/051305 A2 | 6/2005 |
| WO | WO-2006/014597 A1 | 2/2006 |
| WO | WO 2006/032847 A1 | 3/2006 |
| WO | WO 2006/047868 A1 | 5/2006 |
| WO | WO 2006/072243 A1 | 7/2006 |
| WO | WO-2006/125650 A1 | 11/2006 |
| WO | WO 2006/135344 A1 | 12/2006 |
| WO | WO 2007025244 A2 | 3/2007 |
| WO | WO 2007/080453 A2 | 7/2007 |
| WO | WO 2008/011707 A1 | 1/2008 |
| WO | WO-2008/013962 A2 | 1/2008 |
| WO | WO-2009/089346 A2 | 7/2009 |
| WO | WO 2010/051636 A1 | 5/2010 |
| WO | WO 2010/051641 A1 | 5/2010 |
| WO | WO 2011/006263 A1 | 1/2011 |
| WO | WO-2011/058448 A2 | 5/2011 |
| WO | WO 2011/134087 A1 | 11/2011 |
| WO | WO-2013/155620 A1 | 10/2013 |

OTHER PUBLICATIONS

Alster et al., "Photodynamic therapy: practical cosmetic applications," Journal of Drugs in Dermatology, vol. 5(8); pp. 764-768, XP008147410 (2006).

Colman and Roenigk, "The healing of wounds in the skin of piglets treated with benzoyl peroxide," The Journal of Dermatologic Surgery and Oncology, vol. 4(9), pp. 705-707 (1978). XP 009151883.

FDA, Product Classification Database Search, Device: Eosin y: database updated Jun. 6, 2008.

Goldberg, David J., "Photodynamic therapy in skin rejuvenation," Clinics in Dermatology, vol. 26(6), pp. 608-613, XP025545890 (2008).

Kelly et al., "Combined photodynamic and photothermal induced injury enhances damage to in vivo model blood vessels," Lasers in Surgery and Medicine, vol. 34(5); pp. 407-413, XP008147412 (2004).

McCullach, et al., "Photosensitized destruction of Chlorella vulgaris by methylene blue or nuclear fast red combined with hydrogen peroxide under visible light irradiation," Environ. Sci. Tech, vol. 40, pp. 2421-2425 (2006).

Meisel, et al., "Photodynamic therapy for periodontal diseases: State of the art," Journal of Photochemistry and Photobiology B: Biology, 2005, 79, 159-170.

Publication date of following document established by Internet Archive Wayback Machine<URL: <http://web.archive.org/web/20090208211504/http://en.wikipedia.org/wiki/Eosin_08-02-2009.

"Resources: Fluorochrome Absorption Emission Wavelengths." [Online] XP002449595 Retrieved from the Internet: URL: <http://www.sciencegateway.org/resource>s/fae1.htm>[retrieved on Sep. 6, 2007] see p. 2: Rhoadmine WT emission nm 555 p. 2.

Roy et al., "Dermal Wound Healing Is Subject to Redox Control," Molecular Therapy, vol. 13(1), pp. 211-220 (2006).

Sun, Grace, "Lasers and Light Amplification in Dentistry," retrieved online at http://www.sundds.comllaser/ on Jun. 23, 2005.

Rodgers, William, "Fluorescence Polarization Standards for High-Throughput Screening and Imaging," Bio Techniques, vol. 32, pp. 34-42 (2002).

FDA, Color Additive Status List: http://www.cfsanJda.gov/-dms/opa-appc.html.; FDA, Product Classification Database Search, Device: Eosin y: database updated Jun. 6, 2008. (Re-submitted to include publication date).

Berneburg et al., "Phototherapy with Narrowband UVB," Acta Derm Venereol, 85(1-11) (2005).

Sezer et al., "Topical Drug Delivery Using Chitosan Nano- and Microparticles," Informa UK, pp. 1129-1146, (ISSN 1742-5247 (2012).

Antunes et al., "Evaluation of the clastogenicity and anticlastongenicity of the carotenoid bixin in human lymphocyte cultures," Mutat Res. 585(1-2):113-9 (2005).

Darzynkiewicz e al., "Photosensitizing effects of the tricyclic heteroaromatic cationic dyes pyronin Y and toluidine blue O (tolonium chloride)," Cancer Res., 48(5) 1295-9 (1988).

(56) References Cited

OTHER PUBLICATIONS

De et al., "Environmental effects on the aggregation of some xanthene dyes used in lasers," Spectrochim Acta A Mol Biomol Spectrosc., 61(8) 1821-33 (2005).

Jankowski et al., "The action of photosensitizers and serum in a bactericidal process. II. The effects of dyes: hypericin, eosin Y and saphranine O," Pol J Microbiol., 54(4):323-30 (2005).

Montenegro et al., "Model studies on the photosensitized isomerication of bixin," J Agric Food Chem, 52(2): 367-73 (2004).

Nolan et al., "The efficacy of topical hyaluronic acid in the management of oral lichen planus," Journal of Oral Pathology and Medicine, 38:3, pp. 299-303 (Feb. 23, 2009), XP055103025.

Steinberg et al., "Genetic and Physiological Effects of Noncoherent Visible Light Combined with Hydrogen Peroxide on Streptococcus mutans in Biofilm," Antimicrobial Agents and Chemotherapy, 52:7, pp. 2626-2631, (Mar. 3, 2008) (XP055103315).

Subba et al, "Photocatalytic transformation of dyes and by-products in the presence of hydrogen peroxide," Environ Technol., 24(8) 1025-30 (2003).

* cited by examiner

TEETH WHITENING COMPOSITIONS AND METHODS

REFERENCE TO RELATED APPLICATIONS

This application is a continuation of U.S. application Ser. No. 13/296,007, filed Nov. 14, 2011, which is a continuation of U.S. application Ser. No. 11/598,206, filed Nov. 9, 2006, which claims the benefit of U.S. Provisional Application No. 60/735,072, filed Nov. 9, 2005. The disclosures of each of the foregoing applications are hereby incorporated by reference in their entirety.

FIELD OF THE INVENTION

The present invention relates generally to teeth whitening compositions. More specifically, the invention relates to teeth whitening compositions and kits that can be employed to provide a desired whitening effect (e.g., at least two shades of whitening) in less than 20 minutes (e.g., in about 1 minute) without significant post-treatment sensitivity.

BACKGROUND OF THE INVENTION

Peroxide and peroxyacid compounds, such as hydrogen peroxide and carbamide peroxide, have been disclosed as useful in teeth whitening compositions, Application of UV or visible light from, e.g., Argon lasers, has been employed to accelerate whitening after application of peroxide compositions to the teeth. Additionally, whitening compositions have been described that include compounds capable of absorbing light and converting it to heat or chemical energy, such as the metal-ligand complexes and metal chelate precursors described in U.S. Pat. No. 6,343,933 to Montgomery et al.

Red dyes have also been employed to absorb visible or UV energy and produce heat in a bleaching composition as described, e.g., in U.S. Pat. No. 6,485,709 to Banerjee et al. This patent also describes attempts to further enhance such compositions by adding metal ions, an organo-metallic enzyme (e.g., catalase), or using high pH (e.g., above 7) to destabilize or activate the decomposition of hydrogen peroxide. Teeth whitening compositions have also been described that include violet or blue-violet dyes to counter-stain yellow teeth in U.S. Pat. No. 6,030,222 to Tarver. Rhodamine B dye has been employed in a teeth whitening composition as described in WO 02/22097 to Verheyen et al.

Tooth sensitivity following treatment, and the time required for teeth whitening compositions (typically requiring about an hour of time or multiple applications or both), however, remains a significant drawback.

SUMMARY OF THE INVENTION

The present invention provides novel compositions and methods that whiten teeth in a surprisingly short amount of time (e.g., about 1 to 10 minutes) and with minimal or no sensitivity post-treatment. The invention is based, in part, on the discovery that the use of the dyes described herein dramatically accelerates the whitening process.

Without wishing to be bound to any particular theory, it is believed that inclusion of these dyes significantly enhances the compositions of the invention at least because it is believed that dentin transmits green light and absorbs blue light. Accordingly, the dyes of the present invention enhance whitening not only at the surface of the tooth, but also may be transmitting light into the tooth to enhance the alteration of color agents by radicals that have penetrated into the tooth surface.

Another advantage of the present invention is that the compositions can be effective when applied only for a short period of time (e.g., 1 minute in some embodiments). Accordingly, sensitivity due to, e.g., percolation of hydrogen peroxide to the pulp tissue causing (e.g., pulpal inflammation), may be minimized or eliminated. Another advantage of the present invention is that the compositions do not require compounds that generate heat, and therefore, discomfort associated with compositions that generate heat may be minimized or eliminated. Yet another advantage is that dyes can be used (e.g., Eosin B) that are less toxic than dyes such as Rhodamine B.

In one aspect, the present invention features a tooth whitening composition which includes an oxidizing agent and an activating agent having an emission wavelength between about 400 nm and about 570 nm.

In one embodiment, the activating agent is capable of emitting green light, blue light or blue-green light, and/or absorbs green light, blue light or blue-green light. In another embodiment, the activating agent comprises Eosin B, Erythrosin B, or both.

In another embodiment, the composition further includes a stabilizing agent. In one embodiment, the stabilizing agent is sodium acetate.

In one embodiment, the composition further includes a thickening agent. In one embodiment, the thickening agent is silicon dioxide and/or fumed silica having a particle size less than one micron.

In one embodiment, the composition further includes a hydrophilic gelling agent. In another embodiment, the composition further includes an accelerator agent. In some embodiments, the accelerator agent includes sodium perborate.

In one embodiment, the of the composition is between about 8 and about 10.

The invention also features a method for tooth whitening including applying the tooth whitening composition of the present invention to at least one tooth, and exposing the tooth whitening composition to actinic light such that the tooth is whitened at least about one shade. In one embodiment, the tooth is whitened at least about two shades in less than about 10 minutes or in less than about 5 minutes.

In one embodiment, post-treatment sensitivity is insignificant or eliminated.

In one embodiment, the tooth is exposed to the tooth whitening composition for less than 5 seconds per application.

The invention also features a kit for tooth whitening including a tooth whitening composition of the invention and an apparatus for preparing and/or applying the composition.

The invention also features a kit for tooth whitening including a tooth whitening composition of the invention and instructions for determining a composition application time to achieve a desired whitening effect.

The invention also features a method for tooth whitening including at least one application of actinic light and a tooth whitening composition to at least one tooth such that the tooth is whitened at least about two shades with less than about 1 minute of total exposure to actinic light. In one embodiment, the tooth is whitened at least about three shades in less than about 30 seconds. In another embodiment, there is no significant post-treatment sensitivity.

DETAILED DESCRIPTION OF THE PREFERRED EMBODIMENTS

In order to more clearly and concisely describe the subject matter of the claims, the following definitions are intended to provide guidance as to the meaning of specific terms used in the following written description, examples and appended claims.

The term "accelerating agent" refers to any agent capable of accelerating and/or contributing to the completion of radical generation (e.g., sodium perborate).

The term "actinic light" refers to light energy capable of being absorbed by an activating agent.

The term "activating agent" refers to any agent capable of absorbing actinic light. Preferably, the activating agent enhances and/or accelerates the dispersion of light energy, or otherwise enhances and/or activates the decomposition of an oxidizing agent. Activating agents include agents capable of absorbing light energy and emitting light energy, e.g., fluorochromes. Suitable activating agents include, e.g., Eosin B and Erythrosin B.

The term "oxidizing agent" refers to any agent capable of oxidizing, and also includes precursors of compounds capable of oxidizing. Examples of oxidizing agents include, but are not limited to, peroxide, peroxy acid, hydrogen peroxide, carbamide peroxide, alkali metal peroxides, alkali metal percarbonates, peroxyacetic acid, and alkali metal perborates.

The term "post-treatment sensitivity" refers to sensitivity or instant pain experienced by a subject after a tooth whitening procedure. Sensitivity can include, but is not limited to, stimuli such as temperature and pressure. Instant pain typically occurs without stimuli. The terms "significant sensitivity" or "significant post-treatment sensitivity" and the like, refer to significant discomfort post-treatment, including sensitivity and/or instant pain for more than four hours. The term "insignificant pain" refers to minimum sensitivity to stimuli such as temperature and/or pressure for less than four hours post-treatment.

The term "stabilizing agent" refers to any agent that stabilizes one or more agents of the composition (e.g., an oxidizing agent such as hydrogen peroxide). The stabilizing agent can act to stabilize the agent or agents against spontaneous or unwanted reactivity in use and/or in storage. Suitable stabilizing agents include sodium acetate. In some instances, the stabilizing agent can stabilize hydrogen peroxide for about one year.

The term "total exposure to actinic light" refers to the total time a tooth is exposed to actinic light including multiple applications of actinic light over the course of a treatment session.

The term "transparent" refers to a composition capable of at least 70% transmission of light. The term "translucent" refers to a composition capable of at least about 40% transmission of light. The light referred to can be, e.g., actinic light (e.g., from a laser), emitted light (e.g., from a fluorochrome), or both.

The term "translucency agent" refers to any agent capable of increasing the translucency of a composition. Such agents can increase translucency, e.g., upon addition to the composition, upon activation (e.g., by heat, actinic light and/or emitted light), or both.

When ranges are disclosed herein (e.g., wavelength, pH, concentration, particle sizes, and whitening ranges) all individual values and ranges within the disclosed ranges are regarded as part of and encompassed by the present invention. All concentrations are provided in weight % of the composition unless indicated otherwise.

Where "a", "an" or the like is used herein, these articles are used in the open or non-restrictive sense, e.g., to indicate "at least one" or "one or more." Similarly, the term "or" is used in the open or nonrestrictive sense, i.e., to mean "and/or." Accordingly, the terms "or" and "and/or" are used interchangeably and are meant to have the same meaning.

In one aspect, the present invention provides tooth whitening compositions that include an oxidizing agent (e.g., hydrogen peroxide), and an activating agent that has an emission wavelength between about 400 nm and about 570 nm (e.g., Eosin B or Erythrosin B or both). The composition can also include additional agents including, but not limited to, pH adjusting agents, thickening agents, stabilizing agents, accelerating agents, gelling agents, translucency agents.

The oxidizing agent can be any oxidizing agent known in the art. In one embodiment, the oxidizing agent includes hydrogen peroxide or sodium perborate or both. Additionally or alternatively, the oxidizing agent can include carbamide peroxide, alkali metal peroxides, alkali metal percarbonates, alkali metal perborates or combinations of these compounds. The oxidizing agents can be, e.g., liquid, gel, or paste compositions capable of interacting with the activating compound when exposed to actinic light.

The concentration of the oxidizing agent can be varied in the present invention. In one embodiment, the oxidizing composition includes a hydrogen peroxide, e.g., in a range of about 1% to about 70%. In a further embodiment, the oxidizing composition includes about 50% hydrogen peroxide.

The activating agent can include any agent with an emission wavelength between about 400 nm and about 570 nm. In another embodiment, the activating agent emits light in the range of between about 435 nm and about 520 nm. In one embodiment, the activating agent emits light in the range of between about 520 nm and about 565 nm. In certain embodiments, the agent both absorbs and emits light in the above ranges. In one embodiment, the activating agent emits green light. In another embodiment, the activating agent emits blue-green light. In one embodiment the activating agent both absorbs and emits green light.

In one embodiment, the activating agent includes Eosin B or Erythrosine B or both. In another embodiment, the whitening composition includes in the range of about 0.5% to about 0.8%, or between about 0.2% and about 1.2%, or less than about 12%, of Eosin B. In yet another embodiment, the composition includes about 0.2 to about 12% of Eosin B and from about 0.01% to about 0.1%, or about 0.005% and about 0.15%, of Erythrosinc B. Without wishing to be bound to any particular theory it is believed that the combination of Eosin B and Erythrosine B has a synergistic effect. It is believed this synergistic effect may be related to the close absorption peaks of the dyes. It is further believed that because Eosin B and Erythrosine B re-emit green light, that this green light can and may be further absorbed (or re-absorbed) by the fluorochromes so that light energy is not dissipated as in conventional compositions. This absorbed and re-emitted light not only penetrates throughout the bleaching gel, but also is transmitted into the enamel and dentin. Dyes such as Eosin B are also advantageous as they are significantly less toxic than dyes such as Rhodamine B.

Without wishing to be bound to any particular theory, it is believed that because dentin and enamel transmit green light, light in this range can be transmitted into the dentin and/or enamel of the tooth, causing excitation of electrons in specific chemical bonds within the activating agent and tooth chromaphores, making them more susceptible to be attacked by free radicals. The activating agents of the invention can include blue-green and/or blue, emitting dyes. Accordingly, the present invention is based, at least in part, on the discovery that the use of the activating agents of the invention significantly enhance and/or contribute to the enhancement of a whitening effect in a fraction of the time required by conventional compositions. Because the teeth are only exposed to the whitening composition for a fraction of the time as compared to conventional teeth whitening compositions, superficial cracks and crevices, caused by prolonged exposure to free radicals, can be reduced or eliminated. Because decalcification can occur in the cracks and crevices caused by prolonged exposure to free radicals, stains more easily return as the decalcified enamel acts as a sponge. In the present invention, the decreased exposure time to free radicals reduces the possibility of crevices and cracks, thus leading to a significantly prolonged or permanent whitening effect for deeper pigments. Moreover, prolonged periods of exposure cause the enamel to become brittle. It is believed that the composition and methods of the present invention avoid compromise of the enamel.

In one embodiment, the activating agent or agents not only are capable of emitting light in the wavelength range from about 400 nm to about 570 nm, but also absorb light in the wavelength range from about 400 nm to about 570 nm. Such an activating agent is activated by light in the wavelength range of from about 400 nm to about 570 nm. Accordingly, in one embodiment the activating agent absorbs light in the wavelength range of about 400 nm to about 570 nm. In another embodiment, the activating agent absorbs light at a wavelength between about 470 nm to about 550 nm. This embodiment therefore allows for the optimal absorption of energy from the actinic light and the optimal transmission through dentin and enamel.

Without wishing to be bound to any particular theory, it is also believed that activating agents of the present invention, when exposed to actinic light, can accelerate the dispersion of light energy which consequently leads to an instantaneous and complete photochemical activation of the peroxide within the gel. It is believed that the gel mass better transmits light in the wavelength range of about 400 nm to about 570 nm, so that when an activating agent is exposed to actinic light, the dispersion of the light energy leads to an accelerated photochemical activation of the peroxide. Together, these embodiments allow for optimal absorption by the activating agent of energy from the actinic light and the optimal transmission through the composition, dentin and enamel.

In one embodiment, the composition also includes a stabilizing agent. In one embodiment, the stabilizing agent stabilizes the peroxide concentration in the composition for days, weeks, months, a year or several years. In one embodiment, the stabilizing agent not only stabilizes the oxidizing agent, but also is a pH modifier and/or stabilizer. In another embodiment, the stabilizing agent is sodium acetate. In one embodiment, sodium acetate is added until the desired pH is attained. In yet another embodiment, the composition includes between about 0.1% and about 50% stabilizing agent. Any value or range within this range is meant to be encompassed.

In one embodiment, the stabilizing agent is selected from the group consisting of antioxidants such as sodium sulfite, metal chelators (e.g., EDTA), and stabilizers (e.g., tin salts, phosphoric acid, and tin sulphonates). In some embodiments, the stabilizing agent scavenges or otherwise isolates or removes from solution, metal ions that can potentially destabilize the hydrogen peroxide.

In one embodiment, the stabilizing agent is or includes sodium acetate (e.g., sodium acetate trihydrate). Sodium acetate has been found to inhibit spontaneous reactivity of hydrogen peroxide and therefore can provide improved stability.

In one embodiment, the pH of the composition is in or adjusted to the range of from about 4 to about 10. In alkaline conditions, with a pH from about 8 to about 10, the stronger free radical, perhydroxyl ions, can be generated. Perhydroxyl free radicals are capable of reacting not only with yellow and brown stains but even with grey chromophores situated deeper in the tooth structure. In further embodiments, the pH of the composition is between about 5 and about 7, or between about 5 and about 6. In certain embodiments the pH is about 6.

Suitable pH adjusting agents include, but are not limited to, sodium hydroxide, potassium hydroxide, ammonium hydroxide, sodium carbonate, potassium carbonate, TRIS, and triethanolamine, or any other salt of an alkaline base which is safely used in the mouth. In another embodiment, the pH adjusting agent is sodium perborate. In certain embodiments of the invention, a single component may act as a pH adjusting agent or as a stabilizing agent or may serve both functions. In one embodiment, sodium acetate acts as a pH adjusting agent and as a stabilizing agent. In further embodiments, the pH adjusting agent is of the group consisting of sodium bicarbonate, calcium bicarbonate, sodium carbonate and calcium carbonate.

Additionally or alternatively, the composition can include a thickening agent to improve the ease of application of the composition to the teeth such that even and effective coverage is more readily achieved. Suitable thickening agents include but are not limited to mixed silica-aluminum oxides, long chain hydrocarbons such as synthetic carborners (e.g., Carbopol), triethanolamine (e.g., Trolamine), and water soluble poly(ethylene oxide) resins (e.g., Polyox). Suitable thickening agents also include amide starches.

It has been found that using an agent which has a particle size in the range from about 0.2 microns (µm) to about 0.7 µm provides for more widespread dispersion of the oxidizing agent on the particle surface. Accordingly, in one embodiment, the activating agent has a particle size below about 2 microns or below about 1 micron. In other embodiments, the agent has a particle size below about 0.8, 0.7, 0.6, 0.5, 0.4, 0.3, or 0.2 microns. In other embodiments, the activating agent has a particle size between about 0.1 and about 0.8, between about 0.2 and about 0.7, or between about 0.3 and about 0.6 microns.

Additionally or alternatively, the thickening agent can include fumed silica and/or any other inert inorganic material that may be used as a carrier and can aid in the delivery of active oxygen to the tooth surface. Fumed silica of a small particle size (e.g., between about 0.2 microns and about 0.4 microns), can provide efficient dispersion of hydrogen peroxide and reflection of light energy within the oxidizing composition.

In some embodiments, the compositions of the invention include a reaction accelerator or accelerating agent. In one embodiment, the composition includes sodium perborate. Sodium perborate has selective reactivity with hydrogen peroxide in forming free radicals (reacts with water to release hydrogen peroxide). The use of one or more activating agents (e.g., sodium perborate) can be advantageous because they can absorb and retain heat generated in the composition by, e.g., actinic light, thus restricting any such heat to the gel in order to accelerate the reaction without heating the tooth, which can cause sensitivity. In addition, acceleration of the reaction means that the composition can be removed more quickly than conventional compositions thereby decreasing exposure of the patient to the composition and resulting sensitivity and/or other damage to tissues and teeth.

In one embodiment, the compositions of the invention include between about 0.8% and about 15%, or between about 0.3% and about 18% accelerator agent.

In further embodiments, the compositions of the invention include a gelling agent. Preferably the gelling agent is also a translucency agent. For example, a hydrophilic gelling agent can be employed to increase the translucency of the resulting composition or gel.

In some embodiments, the nature of the gelling agent (e.g., its hydrophilic nature) prevents vaporization of the gel when exposed to actinic light, thus improving hydration of the coated tooth area. Increased hydration of the teeth and surrounding tissues is associated with decreased discomfort and sensitivity. In one embodiment, the gelling agent can include, for example, one or more modified starches and/or glucose. In one embodiment, modified starches and/or glucose are activated in cold water. In some embodiments, the gelling agent further enhances the consistency of the composition, facilitating the application to the tooth surface.

The translucency agent can enhance translucency or transparency upon addition to the composition and/or upon activation by, e.g., actinic light, emitted light and/or heat. In one embodiment, it minimizes vaporization of the composition. Additionally or alternatively, the gelling and/or translucency agent minimizes any thermal effects by absorbing any heat generated in the composition.

In one embodiment the composition is a translucent composition. In another embodiment the composition is a transparent composition. In certain embodiments, the composition is translucent or transparent to the actinic light it will be exposed to (e.g., green, blue-green or blue light).

In one embodiment, the composition includes an oxidizing agent (e.g., hydrogen peroxide), an accelerating agent (e.g., sodium perborate), an activating agent (Eosin B or Erythrosin B or both), a stabilizing agent (e.g., sodium acetate trihydrate), a pH adjusting agent, a thickening agent (e.g., fumed silica or silicon dioxide or both), and a gelling agent. In one embodiment, the pH of the composition is from about 6 to about 10. In some embodiments, the pH of the composition is from about 8 to about 10.

Another aspect of the invention provides a method for tooth whitening including applying a tooth whitening composition of the present invention to at least one tooth, and exposing the tooth whitening composition to actinic light to activate the oxidizing agent. The composition may be any of the compositions described herein.

In one embodiment, the method for bleaching the teeth is performed in a dentist's office or dental operatory under ordinary conditions. The composition can be mixed chair-side and applied to the surfaces of as many teeth as are desired to be whitened. Alternatively, the composition can be provided without the need for mixing chair-side. Thereafter, the composition can be exposed to actinic light to accelerate decomposition of the oxidizing agent and the formation of free radicals. In one embodiment, premixes can be prepared with some or all of the ingredients and then mixed chairside and applied to the teeth. In one embodiment, a hydrogen peroxide/sodium acetate solution premix can be prepared and stored prior to use. Additionally or alternatively, some or all of the remaining ingredients can also be separately premixed and stored prior to use. Such premixes can be stored, e.g., for at least about one year.

The compositions of the invention can be used to whiten teeth discolored by any agent or disorder. For example, the compositions may be used to whiten discoloration due to stains (e.g., tobacco, coffee, tea and/or food stains), fluorosis, developmental disturbances, bacteria, genetics, tetracycline antibiotics, trauma, blood decomposition, pigments present during development of teeth, etc.

Any source of actinic light can be used and preferably it is capable of emitting light in a wavelength appropriate to the activating agent employed in the composition. In one embodiment, e.g., an argon laser is used. In another embodiment, a potassium-titanyl phosphate (KTP) laser (e.g. a Green-Light™ laser) is used as a light source. In one embodiment the light source emits light at or near the absorption wavelength of the activating agent or at least one of the activating agents, if several are included in the composition.

The most intense fluorescence (e.g., emission) from a fluorochrome dye occurs when it is irradiated with wavelengths close to the peak of the absorption wavelength (i.e., excitation curve). Accordingly, in one embodiment, the actinic light is at a wavelength of about the absorption wavelength of the activating agent. In one embodiment, the actinic light has a wavelength in the range from about 470 nm to about 550 nm. In another embodiment, the actinic light has a wavelength in the range from about 470 nm to about 520 nm. In yet another embodiment, an argon laser provides actinic light in the wavelength range from about 470 nm to about 520 nm. In a further embodiment, the actinic light has a wavelength of about 530 nm to about 535 nm. In still another embodiment, the source of actinic light in the wavelength range of about 530 nm to about 535 nm is a KTP laser. In this embodiment the source is a KTP laser set at about 532 nm. In another embodiment, a photocuring device is the source of actinic light.

In one embodiment, the tooth is exposed to actinic light for less than 20 minutes, in another for less than 10 minutes, in another for less than 5 minutes. In one embodiment the tooth is exposed to actinic light for less than 4, 3, 2, or 1 minute. In one embodiment, the invention provides a method for whitening teeth at least 2 shades in about 1 minute. In some embodiments, there is no significant post-treatment sensitivity. In other embodiments, there is no post-treatment sensitivity.

In one embodiment, the tooth whitening composition is applied and the tooth is exposed to multiple applications of actinic light, for a time of about 4 to about 6 seconds each tooth per exposure. In some embodiments, the tooth is exposed to actinic light at least two, three, four, five or six times. In some embodiments, a fresh application of the tooth whitening composition is applied before each exposure to actinic light. In some embodiments, the total exposure to actinic light is less than about one minute. In other embodiments, the total exposure to actinic light is less than about 60, 40, 30, or 20 seconds.

In one embodiment, the tooth is whitened at least 7 shades, 6 shades, 5 shades, 4 shades, 3 shades, 2 shades or 1 shade. Shades can be determined before and after treatment using any of a number of shade guides, including, e.g., the VITA® (Vita Zahnfabrik H. Rauter GmbH & Co., KG), CHROMASCOP® (Ivoclar Vivadent, Inc.) or BIODENT (Dentsply Internatinal) shade guides. Optionally, a shade taking system, e.g., the ShadeEye NCC Dental Chroma Meter, can be employed to determine shade before and/or after treatment.

In one embodiment, the tooth is whitened at least two shades, three shades, four shades, five shades, six shades or seven shades in less than about one minute of total exposure time to actinic light. In some embodiments, the tooth is whitened at least two shades, three shades, four shades, five shades, six shades or seven shades in less than about 40 seconds of total exposure time to actinic light. In some embodiments, the tooth is whitened at least two shades, three shades, four shades, five shades, six shades or seven shades in less than about 30 seconds of total exposure time to actinic light. In some embodiments, the tooth is whitened at least two shades, three shades, four shades, five shades, six shades or seven shades in less than about 20 seconds or even less than about 10 seconds of total exposure time to actinic light.

In one embodiment, the risk of transient inflammation of the pulp by percolation of hydrogen peroxide is reduced, not significant and/or eliminated. Without wishing to be bound by any particular theory, inflammation of the pulp is thought to be caused by percolation of hydrogen peroxide into the pulp tissue. In some embodiments, the synergistic effect of the activating agents (e.g., Eosin B and Erythrosin B), and the actinic light results in an instantaneous and complete photochemical reaction. Accordingly, exposure of the tooth, the pulp, and/or the surrounding tissues to the oxidizing agent and/or other components in the composition is dramatically reduced.

In yet another aspect, the invention provides a method for tooth whitening comprising application of actinic light and a composition of the invention (any of the compositions described herein) to at least one tooth such that the tooth is whitened at least about two shades in less than about 10 minutes. In another embodiment, the tooth is whitened at least about two shades in less than about 5 minutes, less than about 4 minutes, less than about 3 minutes, less than about 2 minutes or in about 1 minute. In some embodiments, the teeth are whitened at least about 3 shades, 4 shade or 5 shades. In some embodiments, there is no significant post-treatment sensitivity or no post-treatment sensitivity.

In yet another aspect, the invention provides a kit for preparing or applying a tooth whitening composition in accordance with the present invention. In one embodiment, the kit includes an oxidizing agent and an activating agent that has an emission wavelength between about 400 nm and about 570 nm. The composition can be any of the compositions of the present invention. In one embodiment, the composition is not combined, and may optionally include apparatus to combine two or more components or premixes of the composition. In another embodiment the composition does not require any combination (i.e., it is ready to use and does not require any pre-mixing chair-side).

In another embodiment, the kit includes a composition of the invention and directions for application. Additionally or alternatively, the kit can include apparatus for application (e.g., brushes or trays or both). The kit can also include charts or other information helpful in assessing the whitening effect desired and/or achieved by the methods and compositions of the invention. The kit can also include a source of actinic light.

Identification of equivalent compositions, methods and kits are well within the skill of the ordinary practitioner and would require no more than routine experimentation, in light of the teachings of the present disclosure. Practice of the invention will be still more fully understood from the following examples, which are presented herein for illustration only and should not be construed as limiting the invention in any way.

Example 1

Preparation of an Exemplary Whitening Composition and Activation by Actinic Light A premix was prepared by mixing 4 mg of Eosin B, 1 mg Erythrosine B, 450 mg filmed silica, and 45 mg sodium perborate. Separately, the pH of a 50% hydrogen peroxide solution was adjusted to pH 6 using sodium acetate solution. Approximately 4-6 ml of the adjusted hydrogen peroxide solution was then added to the premix in a plastic mixing chamber and immediately applied.

The gel was applied to frontal surface of the teeth of each subject beginning from the frontal anterior incisors, followed by the posteriors, and finally the posterior incisors. The gel was activated by a KTP laser set at a continuous wave of 0.5 watts. The laser was applied to each tooth for 2-3 seconds. During this time, the gel turned from orange-red to transparent and eventually became dull. After 3-4 minutes for two full arches from premolar to premolar, the gel was aspirated, and the teeth were lightly scrubbed with a cotton roll to clean the surface of the enamel. A second coating of gel was applied using fresh gel and activated with the KTP laser as described above. Up to six consecutive applications were performed to achieve the desired whitening effect for each patient. The duration of the sessions typically did not exceed 40 minutes.

Comparative Example 2

Whitening Effect of Composition

A comparative study was conducted on 10 volunteers between an exemplary composition of the present invention and the SMARTBLEACH laser teeth whitening systems, which is a composition comprising Rhodamine B and hydrogen peroxide. The shade of each patient's teeth was recorded prior to application of whitening composition.

Teeth were coated with the composition prepared in Example 1 and exposed to actinic light from a green laser set at 532 nm for one minute for the entire mouth (4-5 seconds per tooth) and then the composition was removed. The comparative composition was applied to the teeth and exposed to light from a green laser set at 532 nm for 30 seconds per tooth and then left on the surface of the tooth for 10 minutes, in accordance with the manufacturer instructions provided with the composition. The comparative composition required at least 3 to 4 applications, for a total duration of about 1.5 hours for the entire mouth. The composition was removed from each volunteer and the teeth were irrigated with water. The teeth were then evaluated using the VITA scale for the whitening effect of the compositions. Patients were also evaluated for any post-treatment sensitivity by asking them to rate the level of pain experience if any.

The Smartbleach™ treatment resulted in a shade change of one to two shades in the yellow group, while the exemplary composition of the present invention resulted in a shade change of 5 shades in the yellow group, e.g., $A_4$ to $B_1$ VITA scale. In the "yellow group" ($A_4$-$A_1$), treatment with the exemplary composition of the present invention resulted in shade changes of 4-5 shades, resulting in shades in the "white group" ($B_1$-$B_2$). Treatment with the exemplary composition for teeth in the "grey" ($C_4$-$C_1$) and "grey-brown" ($D_4$-$D_2$) groups showed changes of 2-3 shades in the first session.

The following evaluation scale of post-sensitivity was used:

| | |
|---|---|
| Level 0 | No sensitivity to thermal stimuli or any kind of pain following treatment. |
| Level 1 | Sensitivity to thermal stimuli that lasts for a few seconds. |
| Level 2 | Pain or discomfort that occurs due to thermal stimuli and lasts for more than one minute. Optional pain treatment with analgesics. |
| Level 3 | Pain or discomfort that occurs automatically, requiring use of analgesics to control the pain. |

Following treatment with the Smartbleach™ system, all ten subjects experienced pain from Level 1 to Level 3. Following treatment with the exemplary composition of the present invention, nine subjects experienced no pain (e.g., Level 0), and only one subject experienced pain of Level 1.

Comparative Example 3

Effect of Actinic Light Source

A study was conducted on 28 volunteers comparing the effect of different actinic light sources in whitening with the composition of Example 1. A prophylactic session was performed on each patient 3-4 days before the bleaching session. The shade of each patient's teeth was recorded prior to application of whitening composition.

Teeth were coated with the composition prepared in Example 1 and exposed to different sources of actinic light: a green laser (KTP) at 532 nm, a blue (argon) laser at 480-414 nm, a photocuring halogen lamp, and a LED photocuring device.

The activation was performed in the different patients for the left or the right sides of their dental arches according to an activation randomization mode. Specifically, a first patient's right side was activated with the 532 nm green laser, while the left side was activated with the 480 nm-514 nm blue-green laser. A second patient's right side was activated with the photocuring halogen lamp, while the left side was activated with the LED photocuring device. A third patient's right side was activated with the 532 nm green laser, while the left side was activated with the photocuring halogen lamp. A fourth patient's right side was activated with the 532 nm green laser, while the left side was activated with the LED photocuring device. A fifth patient's right side was activated with the 480 nm-514 nm blue-green laser, while the left side was activated with the photocuring halogen lamp. A sixth patient's right side was activated with the 480 nm-514 nm blue-green laser, while the left side was activated with the LED photocuring device.

The composition was removed from the teeth of each volunteer and the teeth were irrigated with water. The teeth were then evaluated using the VITA scale for the whitening effect of the compositions.

Activation by different photocuring devices produced comparable results. The speed of activation with the green laser and the blue-green laser was 4-5 seconds per tooth, while the speed of activation with the photocuring devices was about 10 seconds per tooth. Accordingly, a whitening session employing the green laser or the blue-green laser for the entire mouth would typically take approximately 30 minutes, and a session with a photocuring device would typically take approximately 40 minutes.

What is claimed:

1. A composition comprising:
   about 1% to about 70% peroxide;
   Eosin; and
   a carbomer.
2. The composition of claim 1, wherein the composition further comprises an accelerating agent capable of accelerating radical generation.
3. The composition according to claim 1, wherein the composition further comprises a stabilizing agent capable of stabilizing the peroxide.
4. The composition according to claim 3, wherein the stabilizing agent is sodium acetate.
5. The composition according to claim 1, wherein the pH of the composition is between 4 and 10.
6. The composition according to claim 1, wherein the composition does not generate heat upon exposure to actinic light.
7. The composition according to claim 1, wherein exposure to actinic light results in an instantaneous and complete photochemical reaction.
8. The composition according to claim 1, wherein exposing the composition to actinic light causes accelerated photochemical activation of the peroxide.
9. The composition according to claim 1, wherein the peroxide is selected from hydrogen peroxide, sodium perborate, carbamide peroxide, alkali metal peroxide, alkali metal percarbonate, and alkali metal perborate.
10. The composition of claim 1, wherein the peroxide is hydrogen peroxide.

* * * * *